(12) United States Patent
Doe

(10) Patent No.: US 6,798,099 B1
(45) Date of Patent: Sep. 28, 2004

(54) DEVICES, SYSTEMS AND METHODS FOR SENSING TEMPERATURE OF A DRAG CUP IN A RHEOMETER MOTOR

(75) Inventor: Nigel Doe, Horsham (GB)

(73) Assignee: Waters Investment Limited, New Castle, DE (US)

( * ) Notice: Subject to any disclaimer, the term of this patent is extended or adjusted under 35 U.S.C. 154(b) by 0 days.

(21) Appl. No.: 10/617,712

(22) Filed: Jul. 14, 2003

(51) Int. Cl.[7] .............................................. H02K 11/00
(52) U.S. Cl. .................................................. 310/68 C
(58) Field of Search ...................... 310/68 C; 73/54.28, 73/54.32, 54.35

(56) References Cited

U.S. PATENT DOCUMENTS

| | | |
|---|---|---|
| 1,658,950 A | 2/1928 | Stein |
| 2,096,222 A | 10/1937 | Bock |
| 2,382,979 A | 8/1945 | Demb |
| 2,437,194 A | 3/1948 | Harrington |
| 2,703,006 A | 3/1955 | Savins |
| 2,807,160 A | 9/1957 | Asbeck |
| 2,982,132 A | 5/1961 | Mendlowitz |
| 3,435,666 A | 4/1969 | Fann |
| 3,592,060 A | 7/1971 | Lavernman |
| 3,875,788 A | 4/1975 | Mills |
| 3,935,726 A | 2/1976 | Heinz |
| 3,962,907 A | 6/1976 | Peyrouset et al. |
| 3,989,966 A * | 11/1976 | Blank ...................... 310/68 C |
| 4,185,493 A | 1/1980 | Frosch et al. |
| 4,379,775 A | 4/1983 | Bransteter et al. |
| 4,445,365 A | 5/1984 | Selby |
| 4,466,276 A | 8/1984 | Ruyak et al. |
| 4,468,953 A | 9/1984 | Garritano |
| 4,498,023 A * | 2/1985 | Stout ............................ 310/14 |
| 4,524,611 A | 6/1985 | Richon et al. |
| 4,602,501 A | 7/1986 | Hirata |
| 4,612,799 A | 9/1986 | Choi et al. |
| 4,630,468 A | 12/1986 | Sweet |
| 4,633,708 A | 1/1987 | Blommaert |
| 4,643,021 A | 2/1987 | Mattout |
| 4,878,377 A | 11/1989 | Abel |
| 5,040,410 A | 8/1991 | Chu et al. |
| 5,167,143 A | 12/1992 | Brookfield |
| 5,223,227 A | 6/1993 | Zuckerman |
| 5,308,953 A | 5/1994 | Grudzien, Jr. et al. |
| 5,526,681 A | 6/1996 | Selby |
| 5,587,522 A | 12/1996 | Selby |
| 5,777,212 A | 7/1998 | Sekiguchi et al. |
| 6,018,988 A | 2/2000 | Persson |
| 6,153,954 A * | 11/2000 | Uchida et al. ............ 310/68 C |
| 6,164,818 A | 12/2000 | Dick et al. |
| 6,240,770 B1 | 6/2001 | Raffer |
| 6,476,524 B1 * | 11/2002 | Miyamoto et al. ............ 310/12 |
| 6,499,336 B1 | 12/2002 | Raffer |
| 6,588,254 B1 | 7/2003 | Doe |

FOREIGN PATENT DOCUMENTS

| | | |
|---|---|---|
| FR | 2 389 884 | 1/1979 |
| SU | 1392-453 | 4/1986 |
| SU | 1769-083 | 10/1992 |
| WO | WO 94/20832 | 9/1994 |

OTHER PUBLICATIONS

Physica MCR 300, Modular Compact Rheometer Manual, Apr. 1999.

TA Instruments Rheometers Manual, No Date.

* cited by examiner

Primary Examiner—Thanh Lam
(74) Attorney, Agent, or Firm—Shaw Pittman LLP

(57) ABSTRACT

Devices, systems and methods are disclosed for sensing the temperature of a drag cup within a motor of a rheometer. Such a device includes a coil in communication with a source of current and in close enough proximity to a drag cup such that the coil senses the temperature of the drag cup through fluctuations in electrical activity across the coil.

26 Claims, 13 Drawing Sheets

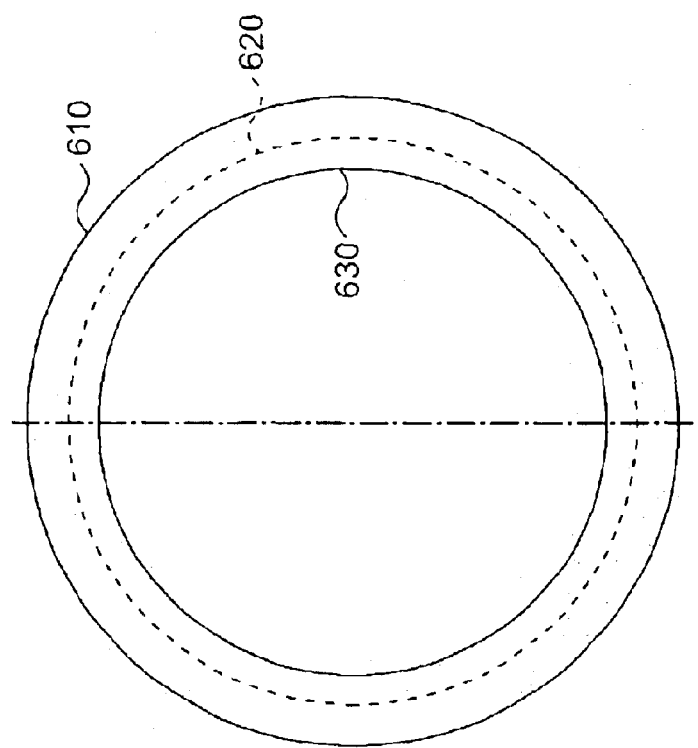
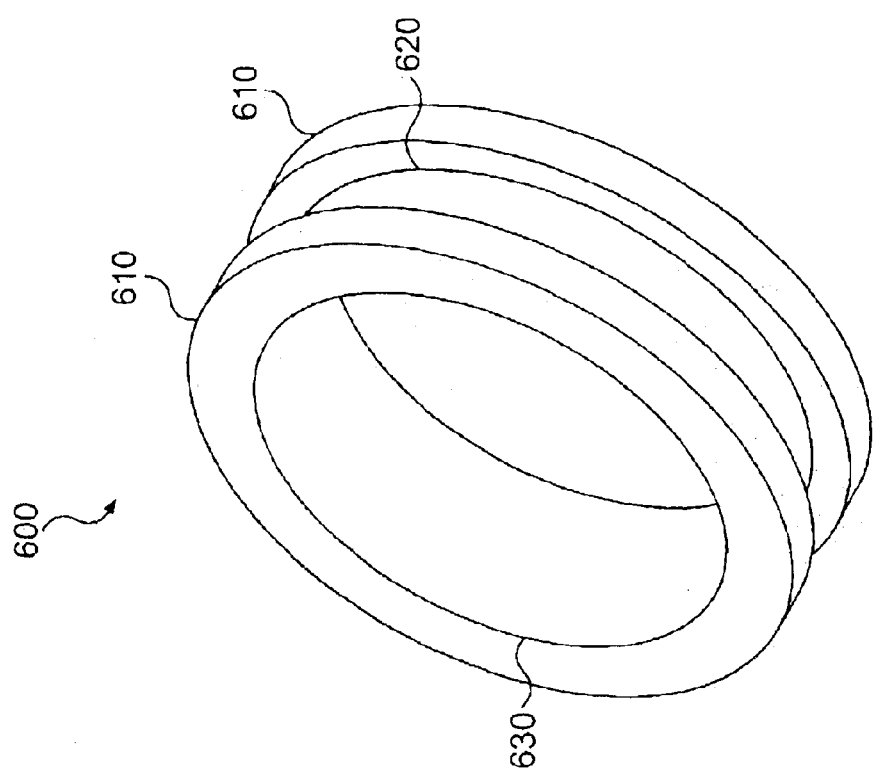

FIG. 8: Non Contact Drag Cup Temperature Measurement - 50% Torque

DEVICES, SYSTEMS AND METHODS FOR SENSING TEMPERATURE OF A DRAG CUP IN A RHEOMETER MOTOR

BACKGROUND

1. Field of the Invention

The present invention relates to devices, systems and methods for sensing temperature. More particularly, the present invention relates to sensing temperature of a drag cup within the motor of a rheometer.

2. Background of the Invention

Rotary rheometers, viscometers or viscosimeters are typically used to measure fluid or other properties of materials, such as their viscosity, compliance, and modulus, by rotating, deflecting or oscillating a measuring geometry in a material, either by applying a torque and measuring the resultant velocity or displacement, or by applying a velocity or displacement and measuring the resultant torque. The torque and velocity/displacement are used in conjunction with measuring geometry factors to determine the properties of the material.

As used herein, the term "rheometer" includes rheometers, viscometers, viscosimeters and similar instruments that are used to measure the properties of fluid or similar materials (see list below).

The term "material," as used herein, includes liquids, oils, dispersions, suspensions, emulsions, adhesives, biological fluids, polymers, gels, pastes, slurries, melts, resins, powders or mixtures thereof. Such materials are also referred to herein as "fluids." More specific examples of materials include asphalt, chocolate, blood, drilling mud, lubricants, oils, greases, photoresists, liquid cements, elastomers, thermoplastics, thermosets and coatings.

A common use for a rheometer is to determine fluid properties of a material. One technique is to apply a torque developed by a drag cup motor in the presence of the material, and measure the resultant velocity or displacement. The torque and velocity/displacement are used in conjunction with measuring geometry factors to determine the properties of the material. It is well known that the torque output of a drag cup motor is dependent on the temperature of the drag cup. For that reason, it is important that the temperature of the drag cup used in the rheometer is known so as to account for an accurate torque measurement used to determine the physical property of the material. If the temperature of the drag cup were not taken into consideration, the accuracy and validity of the measurement of the property of the material would be compromised. Thus it is desirable to measure the temperature of the drag cup to determine its effect on torque.

Despite efforts to maintain a constant and homogenous temperature in the drag cup of a drag cup motor of a rheometer, the actual temperature of the drag cup may fluctuate as it operates thereby affecting the torque output of the motor. Thus, it is desirable to measure the actual temperature of the drag cup as accurately as possible. However, there are difficulties in measuring the actual temperature of the drag cup. For example, one prior art method is to mount a temperature probe in the stator windings of the motor. However, because of a significant air gap between the drag cup and winding, the resulting measurement is likely to be erroneous.

There is, accordingly, a need to develop effective and accurate devices, systems and methods of determining the temperature of a drag cup within a drag cup motor of a rheometer. Furthermore, there is a need to determine the actual temperature of the drag cup in the motor during a time period of a test so as to account for various fluctuations in temperature and their effects on the real-time torque being applied to the material being tested. There is also a need for a flexible yet economic way of measuring the temperature of a drag cup within a rheometer drag cup motor without directly contacting the drag cup or otherwise disrupting its motion within the motor.

SUMMARY OF THE INVENTION

The present invention, as described in the exemplary embodiments presented herein, addresses the inefficiencies and inaccuracies that typically occur when estimating the temperature of a drag cup within a drag cup motor of a rheometer. The exemplary embodiments of the present invention provide devices, systems and methods wherein a temperature-sensing component used to calculate the temperature of the drag cup is maintained inside of the motor and in close proximity to motor components without disturbing the motion of the motor.

In its essence, the present invention senses the temperature of a drag cup of a drag cup motor. This temperature, when properly estimated, is then used to adjust/compensate the actual output torque of the motor when testing a given material. The torque is used directly in the determination of the physical property of the given material. Thus, the present invention is used to fine tune and enhance the determination of the physical property of the given material by taking into account that the drag cup within a drag cup motor gets warm during operation, and such heat affects the estimated torque output of the rheometer.

In a preferred embodiment, a drag cup motor is modified to include a coil in communication with a source of current. The coil is arranged to be located in close enough proximity to the drag cup such that the coil can sense the temperature of the drag cup through fluctuations in electrical activity across the coil.

In another exemplary embodiment of the present invention, a device is disclosed for determining the temperature of a drag cup in a drag cup motor of a rheometer. The device includes means for sensing temperature, wherein the means for sensing temperature is in contact with a source of current and is in close enough proximity to the drag cup such that the means for sensing temperature senses the temperature of the drag cup through fluctuations in electrical activity.

In yet another exemplary embodiment of the present invention, a system is disclosed for determining a property of a material. The system includes a rheometer having a drag cup motor, and a coil in communication with a source of current. The drag cup is in close enough proximity to the coil such that the coil senses fluctuations in electrical activity across the coil.

The features and advantages of the present invention will be more fully appreciated upon a reading of the following detailed description in combination with the accompanying drawings.

BRIEF DESCRIPTION OF THE DRAWINGS

FIGS. 6a–6b are schematic diagrams of different views of a coil former according to an exemplary embodiment of the present invention.

DETAILED DESCRIPTION OF PREFERRED EMBODIMENTS

Figure 1A:
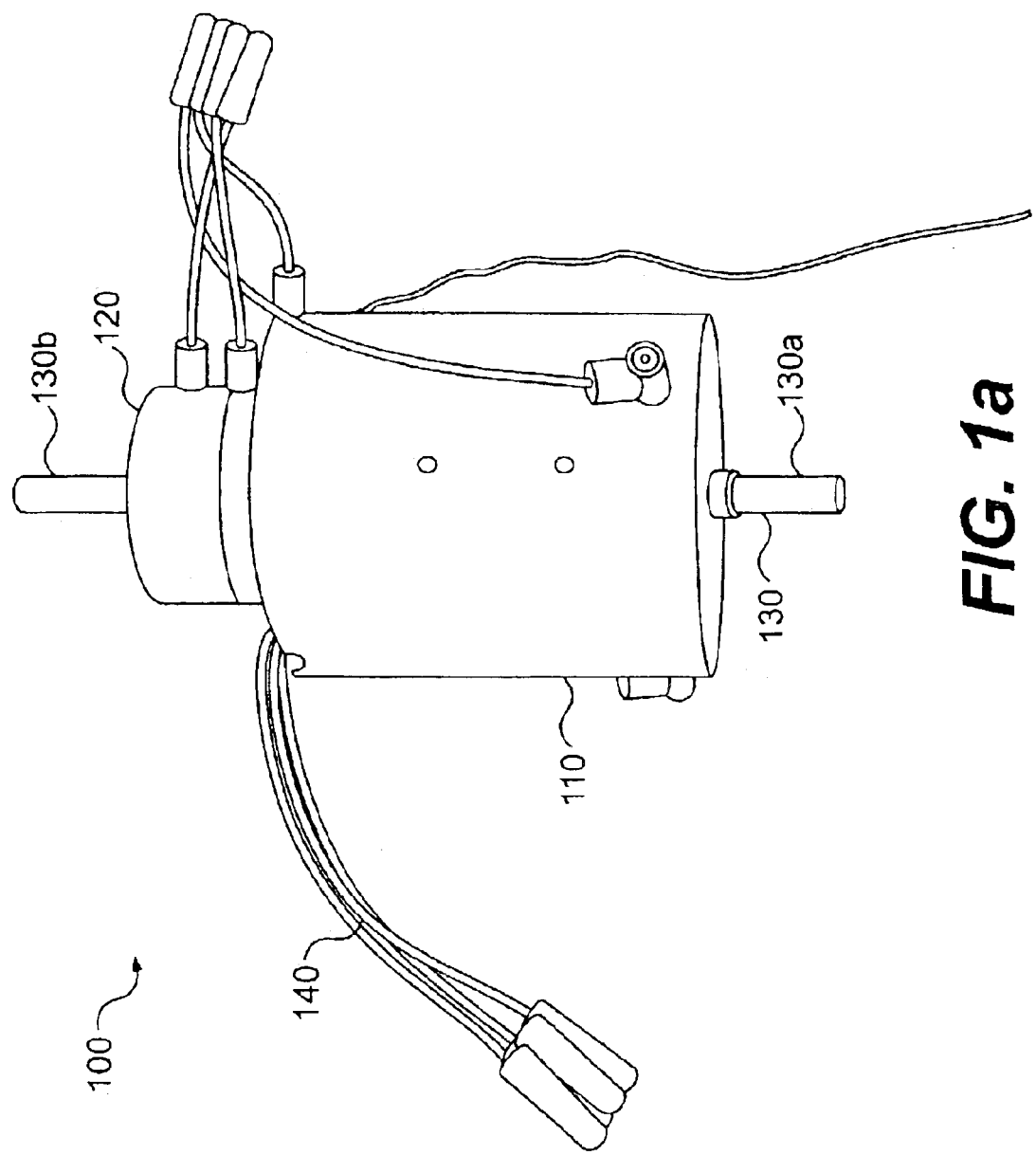
FIG. 1a is a schematic diagram of a drag cup motor according to an exemplary embodiment of the present invention.
Figure 1C:
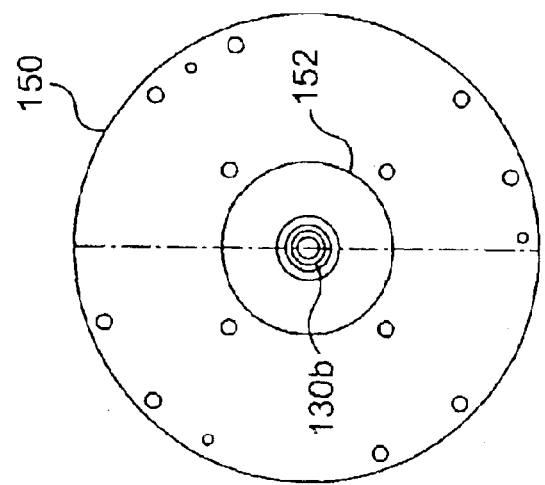
FIG. 1c is a schematic diagram of an end view of the exemplary drag cup motor shown in FIG. 2b.
Figure 1B:
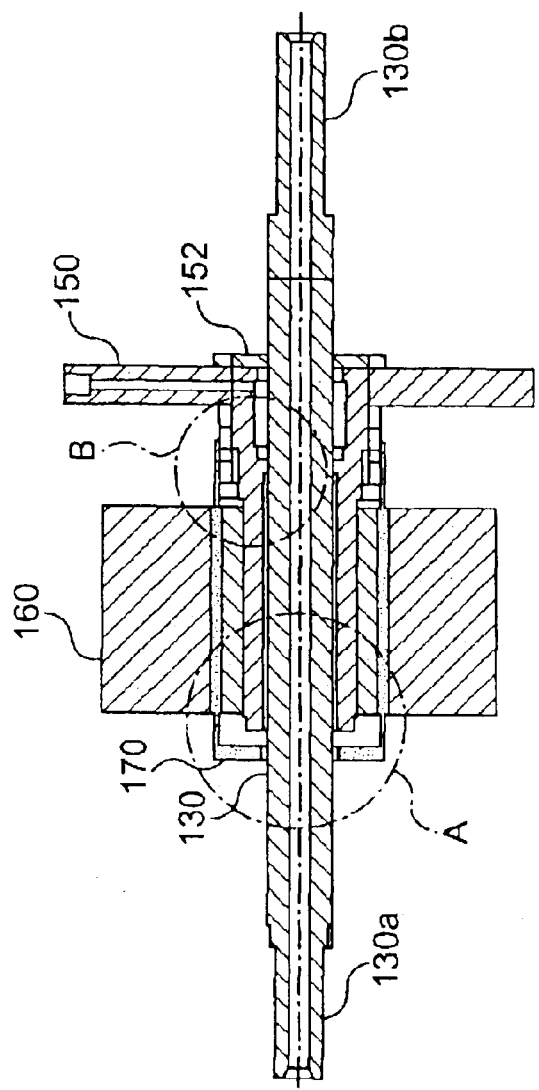
FIG. 1b is a schematic diagram of a cross section of a drag cup motor according to an exemplary embodiment of the present invention.
Figure 1E:
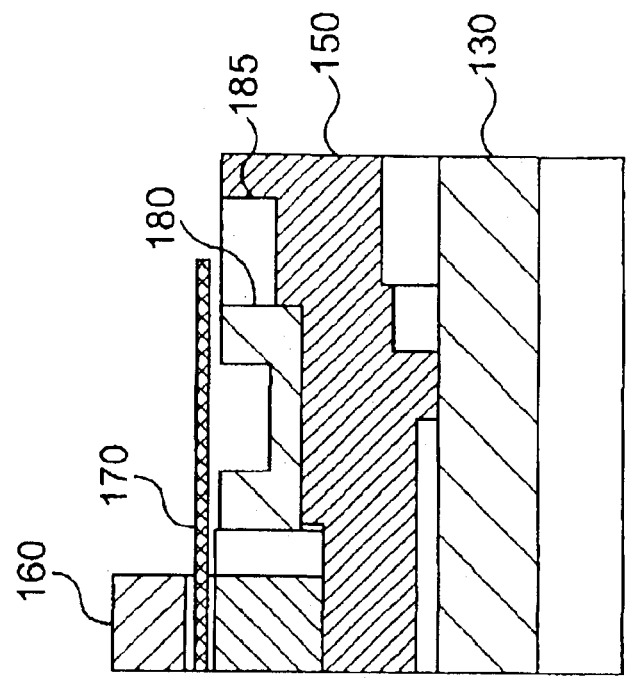
FIG. 1e is a schematic diagram of a more detailed view of circle B of the exemplary drag cup motor shown in FIG. 1b.
Figure 1D:
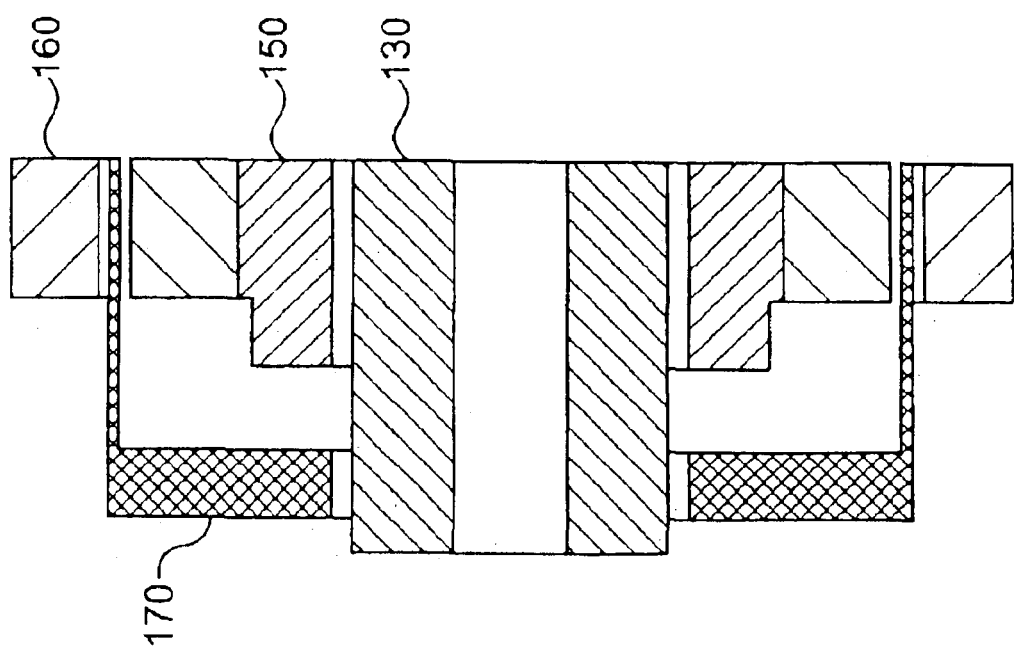
FIG. 1d is a schematic diagram of a more detailed view of circle A of the exemplary drag cup motor shown in FIG. 1b.

The devices, systems and methods according to the present invention facilitate the measurement of temperature of the drag cup within a drag cup motor often used in conjunction with a rheometer. Using evaluative electronics in conjunction with an embedded temperature sensing component, the temperature of the drag cup is easily and accurately measured through the analysis of local eddy currents. The temperature sensing component minimizes the impact on the motor being tested while maximizing the proximity of the measurement location to the drag cup.

Various rheometers may benefit from the teachings of the present invention. Exemplary rheometers include, for example, those described in U.S. patent application Ser. No. 10/108,351, "Rotary Rheometer," filed on Mar. 29, 2002 by Peter Foster and Nigel Doe; and U.S. patent application Ser. No. 10/382,589, "System and Method for Automatic Identification of a Detachable Component of an Instrument," filed on Mar. 7, 2003, by Nigel Doe and Peter Foster. Both of these patent applications are incorporated by reference herein in their entirety. Such exemplary rheometers and others may benefit from incorporating the exemplary embodiments of the present invention within, them or modifying their geometry so as to utilize such novel temperature sensing components and related electronics so as to improve the measurement of actual output torque depending on the measured temperature of the drag cup within the motor utilized.

An exemplary embodiment of a system according to the present invention is shown in FIG. 1 as drag cup motor 100.

Although rheometer motor 100 is shown having a particular shape and geometry, the present invention is not limited to motors having such an exemplary shape or geometry. Other shapes and geometries are possible, apparent to one having ordinary skill in the art and within the purview and scope of the present invention.

Motor 100 includes electrical connectors 140 that connect motor 100 to drive electronics. A main drive shaft 130 of motor 100 has two ends, bottom projection end 130a and top projection end 130b. Air bearings in housing 120 provide proper rotary motion of internal components that effectuate a viscosity measurement of the material being tested. Outer housing 110 protects the internal components of motor 100, serves as barrier to the sensitive internal components of the motor, and acts as container and transporter of the motor components held within.

FIGS. 1b–1e show the internal sensor assembly structure of a drag cup motor, such as motor 100 of FIG. 1a with outer housing 110 having been removed. Such internal structure is merely exemplary and is not intended to be limiting of the present invention. Within the internal structure, a drag cup 170 is positioned such that it may have rotary motion within the motor body. A material (not shown) is tested by measuring the torque necessary to move drag cup 170 and main drive shaft 130 with respect to a motor core holder 150. Furthermore, the motor core holder 150 houses a temperature sensing component 180 that, in conjunction with evaluative electronics, serves to measure the temperature of the drag cup 170. Additional description and details of the drag cup 170, motor core holder 150, temperature sensing component 180 and evaluative electronics will be provided below.

Stator windings 160 encircle the outer portion of drag cup 170, and create the necessary driving force required to operate the rheometer motor 100. Such windings 160 may be constructed of, for example, coils of wire wound around magnetic iron pole pieces or the like.

In an exemplary embodiment, cylindrical main drive shaft 130 having end portions 130a and 130b, and cap portion 152 are all a unitary structure and drag cup 170 is attached to the unitary structure to form an overall unit. This entire unit, as a whole, comprises part of the motor that rotates during operation. Main drive shaft 130, having ends 130a and 130b, fits within motor core holder 150 in such a manner that a cap portion 152 of the cylindrical main drive shaft 130 communicates with the motor core holder 150 and maintains its position therein through support by an air bearing.

A temperature sensing component used in conjunction with evaluative electronics according to a preferred embodiment of the present invention is shown as coil former 180. This exemplary coil former 180 is positioned on motor core holder 150 and is shaped to cradle a coil of wire (not shown) that communicates with evaluative electronics to sense the temperature of drag cup 170 within motor 100. A notch 185 may be used as an exit slot for the wire. Coil former 180 should preferably be constructed of an electrically non-conductive material, such as, for example, heat-resistant rubber or plastic, so as to insulate the coil from eddy currents in other metal components. As shown in FIGS. 1b–1e, coil former 180 is shaped with a "U" cross-section, as an example, to facilitate sensing temperature from substantially the drag cup 170. However, other shapes may also be used, such as, for example a semi-circle or triangular cut, to achieve the same purpose.

Figure 2:
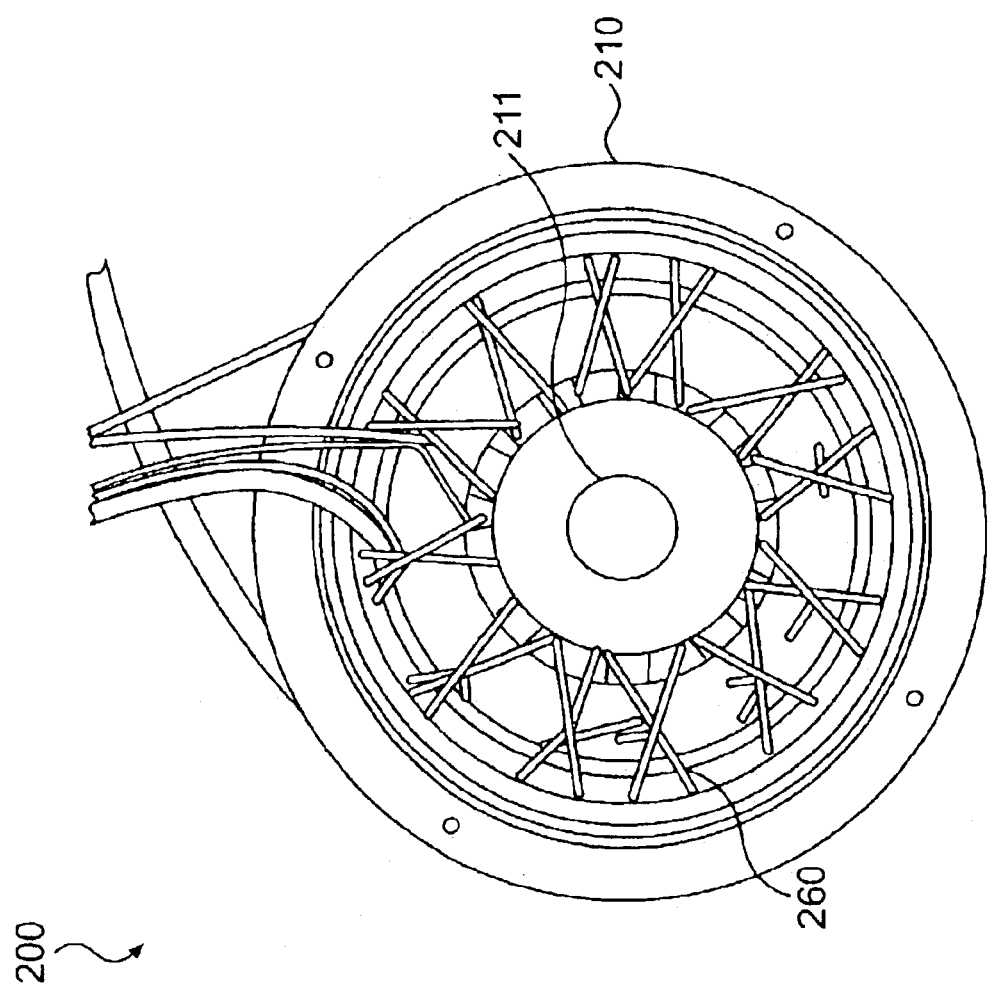
FIG. 2 is a schematic diagram of a top view of an outer body and internal stator windings of a drag cup motor according to, an exemplary embodiment of the present invention.

FIG. 2 shows a top portion of a drag cup motor 200 with a motor core holder having been removed. Internal windings 260 are visible within housing 210. A projection accommodating structure 211 that mates with base projection 130a is shown at a base portion of motor 200 that houses the sensor assembly within and maintains structural stability during rotation.

One of the advantages of the present invention lies in using the internal structure of the motor itself in maximizing the accuracy in temperature measurement of the drag cup. Conventional drag cup motor designs have incorporated temperature sensors in windings 260 of the stator and have used the output of such sensors to correct current flow into windings 260 and therefore the output torque of the motor. A drawback of this conventional method is that an air gap between the stator and the drag cup exists such that such correction is second-order at best. Devices, systems and methods according to the present invention more accurately measure the drag cup temperature directly, thus decreasing errors and inaccuracies attributable to such air gaps and thereby increasing the accuracy of the output torque measurement of a rheometer.

Figure 3A:
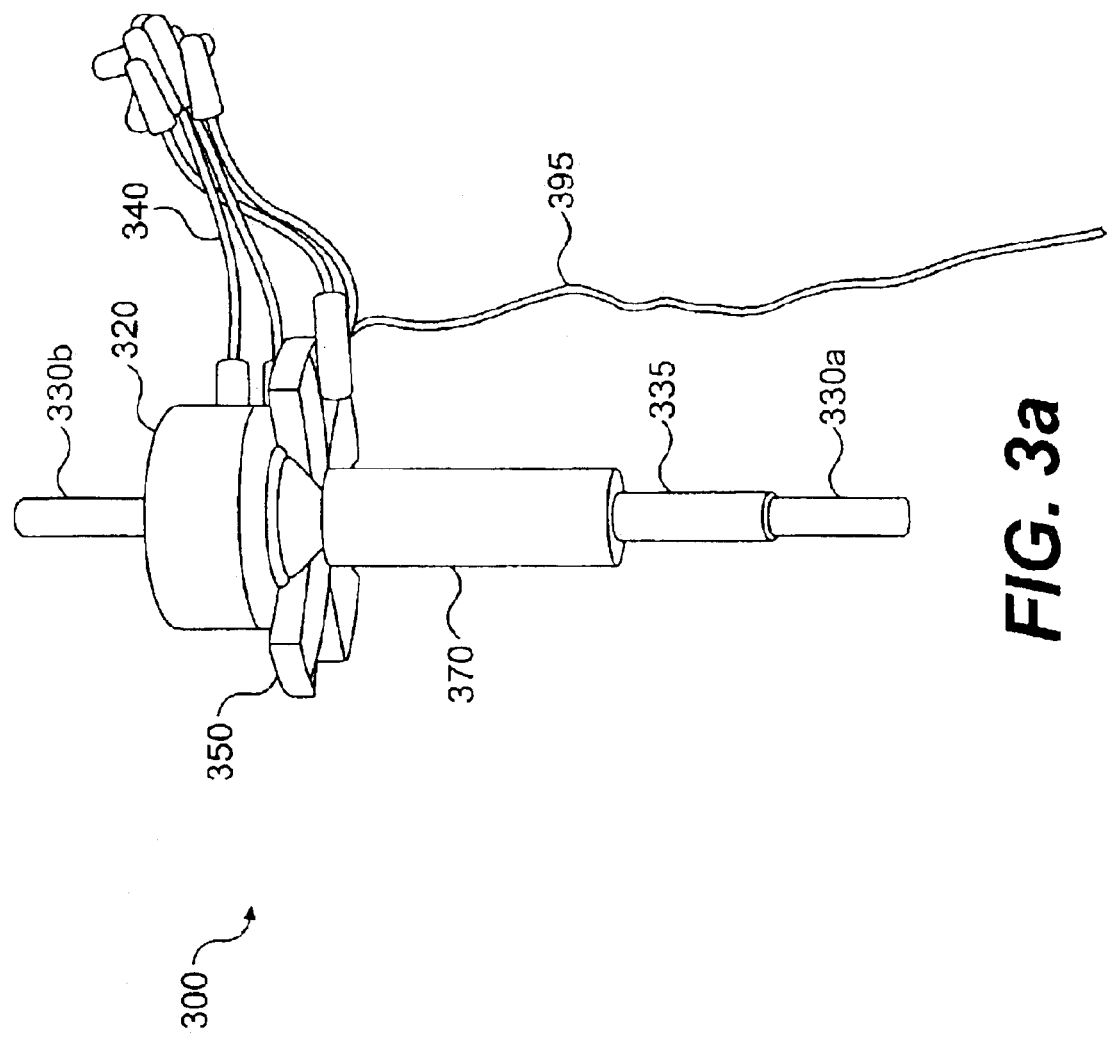
FIG. 3a is a schematic diagram of a drag cup on a motor core holder according to an exemplary embodiment of the present invention.
Figure 3B:
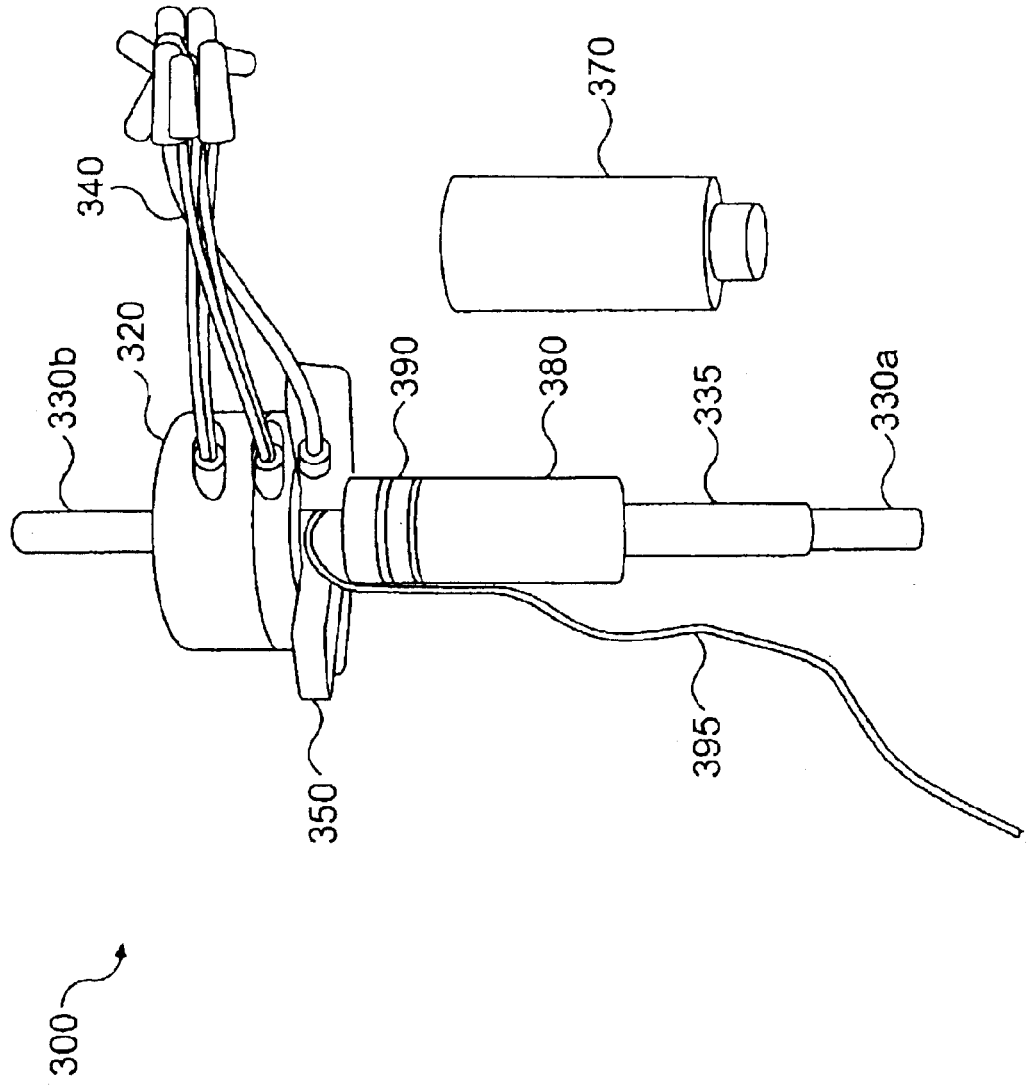
FIG. 3b is a schematic diagram of the motor core holder of FIG. 3a with the drag cup having been removed.
Figure 4B:
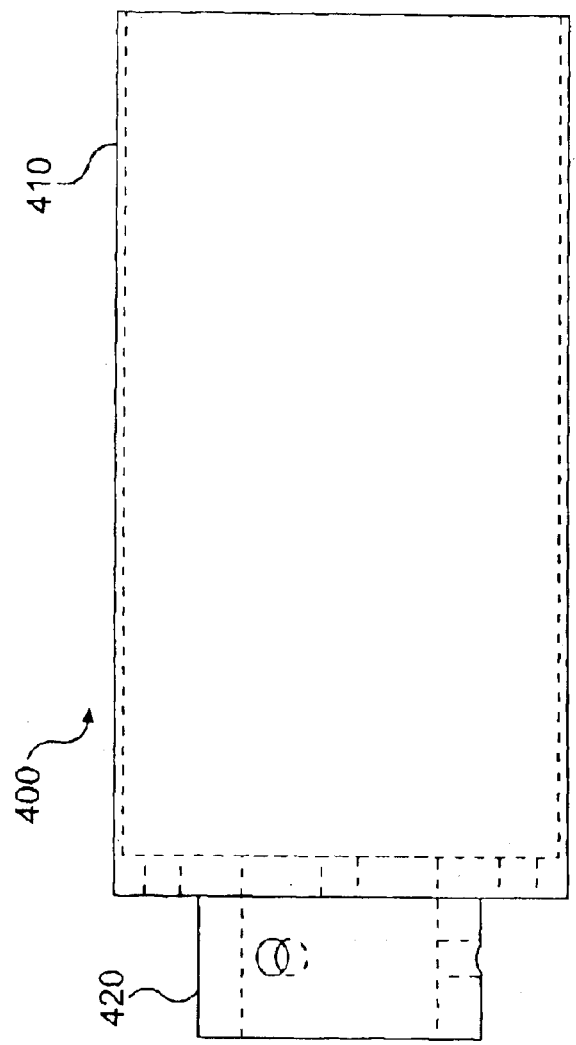
FIGS. 4a–4d are schematic diagrams of different views of a drag cup according to an exemplary embodiment of the present invention.
Figure 4A:
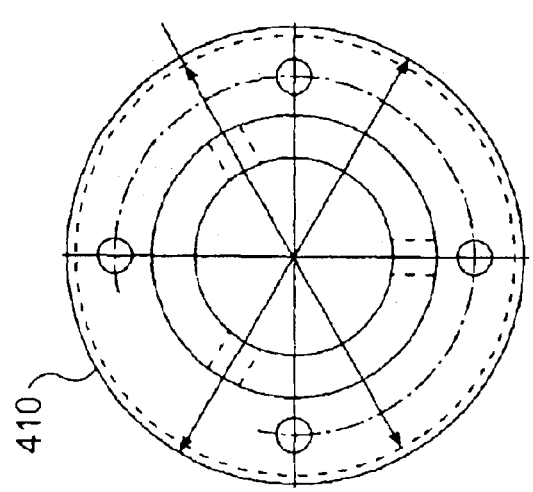
Figure 4D:
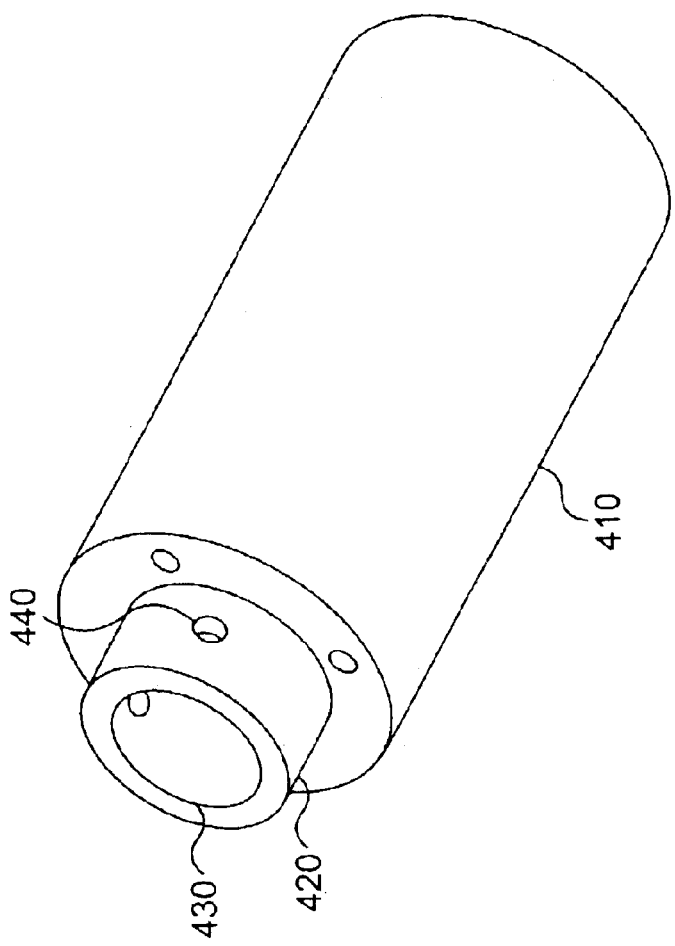
Figure 4C:
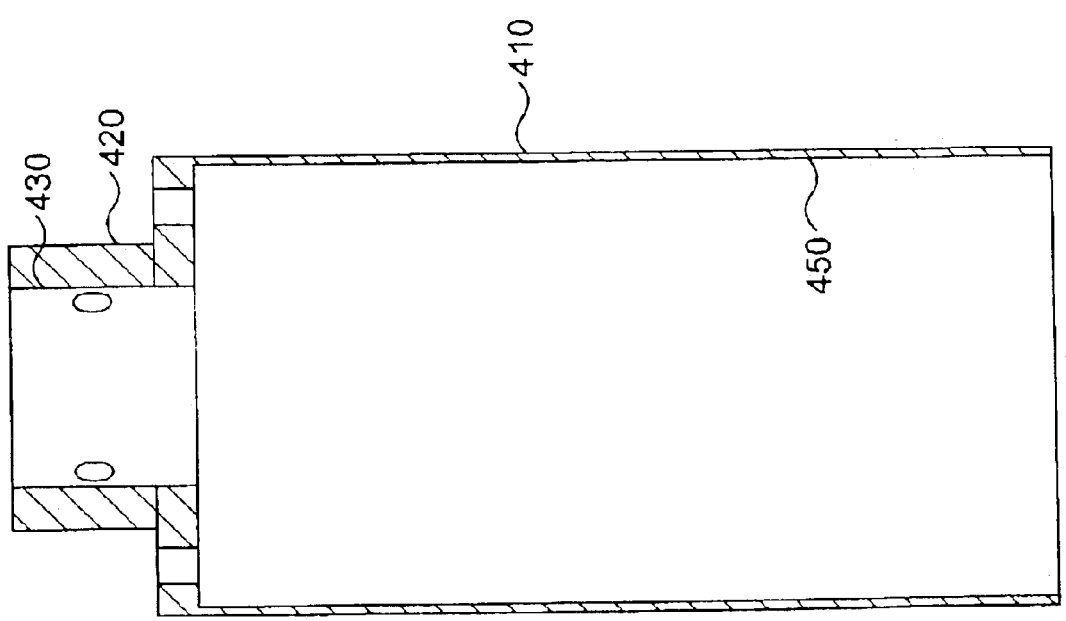

Motor core holder 300, as shown in FIGS. 3a–3b includes an air bearing housing 320 for rotating drag cup 370 with respect to other internal components of a motor. Motor core holder 300 has various air connectors 340 that provide air for the air bearing housing 320. An outer cap 350 allows for a secure fit of motor core holder 300 with respect to a top opening of motor housing 110, as shown in, for example, FIG. 1a.

Rotation motion of the internal components of a drag cup motor are known to one having ordinary skill in the art. Briefly, a rotating magnetic field generates a force in the metal drag cup by inducing an eddy current in the metal cup. The current, in turn, produces its own magnetic field and the two resulting magnetic fields are opposed, according to Lenz's Law. The "cup" field is forced to follow the rotating field. Hence the cup is "dragged" round with the rotating field, thereby generating torque whether the cup moves or not. The speed of rotation of the magnetic field is fixed by the drive frequency and number of poles, and torque can be varied by changing the strength of the field by varying the current through each set of poles. Typically, there are two independent sets of windings in, for example, a two pole motor. Such torque is the product of current in each phase.

During operation, the rotating field rotates at, for example, thousands of revolutions per minute. However, the field may be varied over a very wide range. The combination of very small field strength and high field speed is what gives the drag cup motor its relatively smooth torque at low speed and low torque.

When drag cup 370 is removed from motor core holder 300, temperature sensing component 390 is exposed. Thus, in the exemplary embodiment shown herein, temperature sensing component 390 is positioned underneath drag cup 370. However, other positions are possible and apparent to one having ordinary skill in the art. For example, temperature sensing component 390 could also be positioned outside of drag cup 370. Also, in the example shown, temperature sensing component 390 is positioned relatively high upon the core of the motor shaft cylindrical body 335. However, the position of temperature sensing component 390 is not limited to such a relatively high position and may be positioned anywhere such that drag cup temperature can be effectively measured. For example, temperature sensing component 390 may be positioned in a middle portion of motor core holder 380 rather than near a top portion, as shown in the example of FIG. 3b.

In the exemplary embodiments of the present embodiment as shown in the figures, a temperature sensing component, such as component 390, is shown in close proximity to a drag cup, for example, drag cup 370 in FIGS. 3a–3b. With such positioning, temperature changes in the drag cup of a working motor can be more easily and accurately detected. The torque output from a drag cup motor depends on the magnitude and frequency of the drive current in the stator, and resistance of the drag cup 370. However, drag cup motors are inefficient and can get undesirably hot during operation. Thus, an increase in temperature results in an increase in resistance, leading to a change in torque for a given current. By accurately detecting the temperature of the drag cup 370, the current can be corrected to maintain the torque at a given value. More specifically, in accordance with the present invention, when the drag cup motor is operating, a constant current or voltage is supplied to the coil (through, for example, electrical wire 395), which is wound adjacent an internal periphery of the drag cup. Changes in torque due to changes in temperature of the drag cup can be determined by sensing fluctuations in electrical activity (e.g., voltage or current for applied current or voltage, respectively) across the coil caused by changes in temperature of the drag cup. Winding current or voltage can then be adjusted to compensate for the changes in torque.

An exemplary drag cup 400 is shown in FIGS. 4a–4d. Although drag cup 400 is shown with a given shape and dimension, this example is not limiting of the invention. Other shapes and dimensions are possible and apparent to one having ordinary skill in the art as long as such drag cups perform the same function as described herein. Drag cup 400 is typically in the shape of a substantially circular cylinder although other shapes are possible. Further, drag cup 400 has an outer shell 410 and a cylindrical extension 420 extending from outer shell 410 that acts as a mounting hub 430 and allows attachment to a shaft. Cylindrical extension 420 includes one ore more mounting ports 440 that facilitate attachment of the drag cup 400 to the shaft or other components.

Outer shell 410 tends to be relatively thin as compared to cylindrical extension 420 used for mounting. The drag cup 400 tends to be relatively thin to keep the inertia low. In a preferred embodiment of the present invention, inner surface 450 of outer shell 410 is in close proximity to a temperature sensing component as shown in the figures. Inner surface 430 of cylindrical extension 420 is located far from a temperature sensing component and therefore does not significantly influence the reading of the temperature sensing component unless the temperature sensing component is located in proximity to it. Thus, different materials may be used to construct the wall and/or to line the inner surface of the inner surfaces depending on their proximity to the temperature sensing component.

Figure 5A:
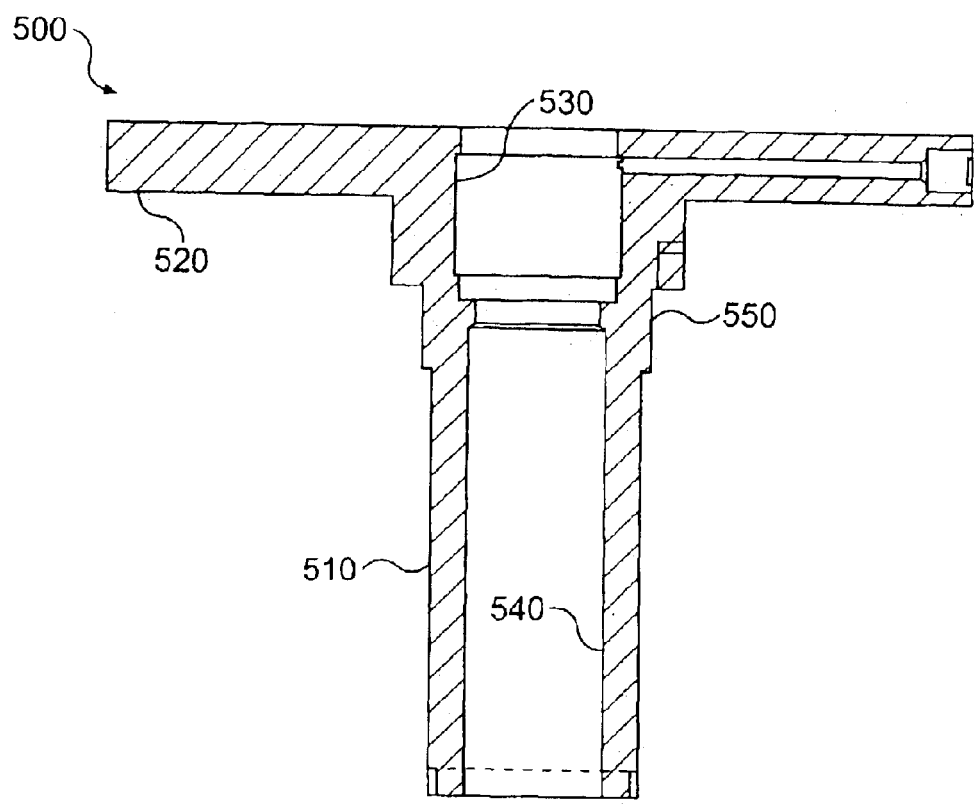
FIGS. 5a–5c are schematic diagrams of different views of a motor core holder according to an exemplary embodiment of the present invention.
Figure 5B:
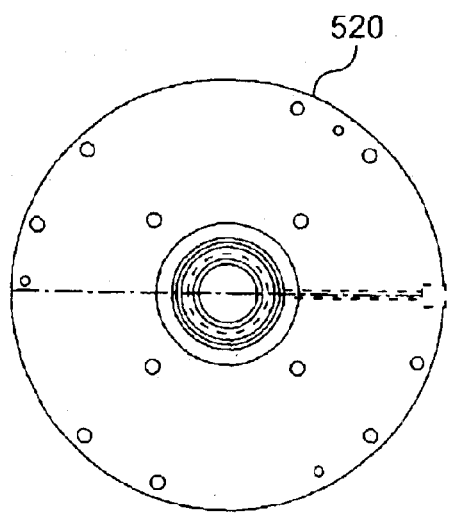
Figure 5C:
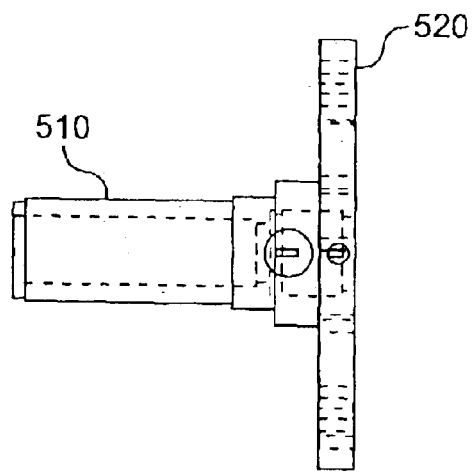

An exemplary embodiment of motor core holder 500 is shown in FIGS. 5a–5c. Motor core holder 500 includes an outer cap 520 that is shaped to lay against a top receiving area (not shown) of outer housing 110, such as shown in FIG. 1a, and more clearly shown in FIG. 2. A body portion 510 extends in a perpendicular direction from a longitudinal axis of outer cap 520 and is shaped to fit within windings of a motor, such as windings 260 of motor 200 shown in FIG. 2. A top inner surface 530 of motor core holder 500 is shaped to accommodate a portion of a radial air bearing therein, such as shown in FIGS. 1a, 3a and 3b. A bottom inner surface 540 of motor core holder 500 is shaped to accommodate a cylindrical body, such as cylindrical body 335 shown in FIG. 3b.

A coil former accommodating area 550 is located in a junction area between outer cap 520 and body portion 510. This accommodating area 550 accommodates a temperature sensing component used in exemplary embodiments of the present invention. Although accommodating area 550 is shown in a particular position in FIGS. 5a–5c, the present invention is not limited to such a position, and one having ordinary skill in the art would position such accommodating area anywhere with respect to a drag cup that would enable a proper detection of drag cup temperature.

As explained above, a drag cup motor incorporating a temperature sensing component according to the present invention provides a more accurate actual output torque by adjusting, for example, the current flowing through the motor to maintain a constant pre-determined torque level.

An exemplary temperature sensing component used in conjunction with evaluative electronics in accordance with a preferred embodiment of the present invention is shown as coil former 600 in FIGS. 6a and 6b. Exemplary coil former 600 includes two outer rims 610 that form an inner coil accommodating area 620. A coil (not shown), which may be constructed of copper wire, may be wound around inner coil accommodating area 620 such that the coil is surrounded by three sides by portions of coil former 600 and exposed on its fourth side to a drag cup in close proximity thereto. Such a coil former 600 is preferably constructed of heat-resistant rubber or plastic. Inner surface 630 of coil former 600 connects with, adheres to, or otherwise fits snugly with coil former accommodation area 550 as shown in FIGS. 5a–5c.

Although exemplary coil former 600 is shown with a particular shape, the present invention is not limited to such shape. Other shapes, such as, for example, semi-circular cross-section or triangular cross-section may be used in lieu of the rectangular cross-section of inner coil accommodating area 620 shown in FIG. 6a. Furthermore, the coil, which is positioned close to the circumference of (he cylindrical drag cup, may be positioned inside or outside of a drag cup. Although the coil is in close proximity to a drag cup, it should not touch the drag cup so as to avoid interference with motor operation.

Figure 7:
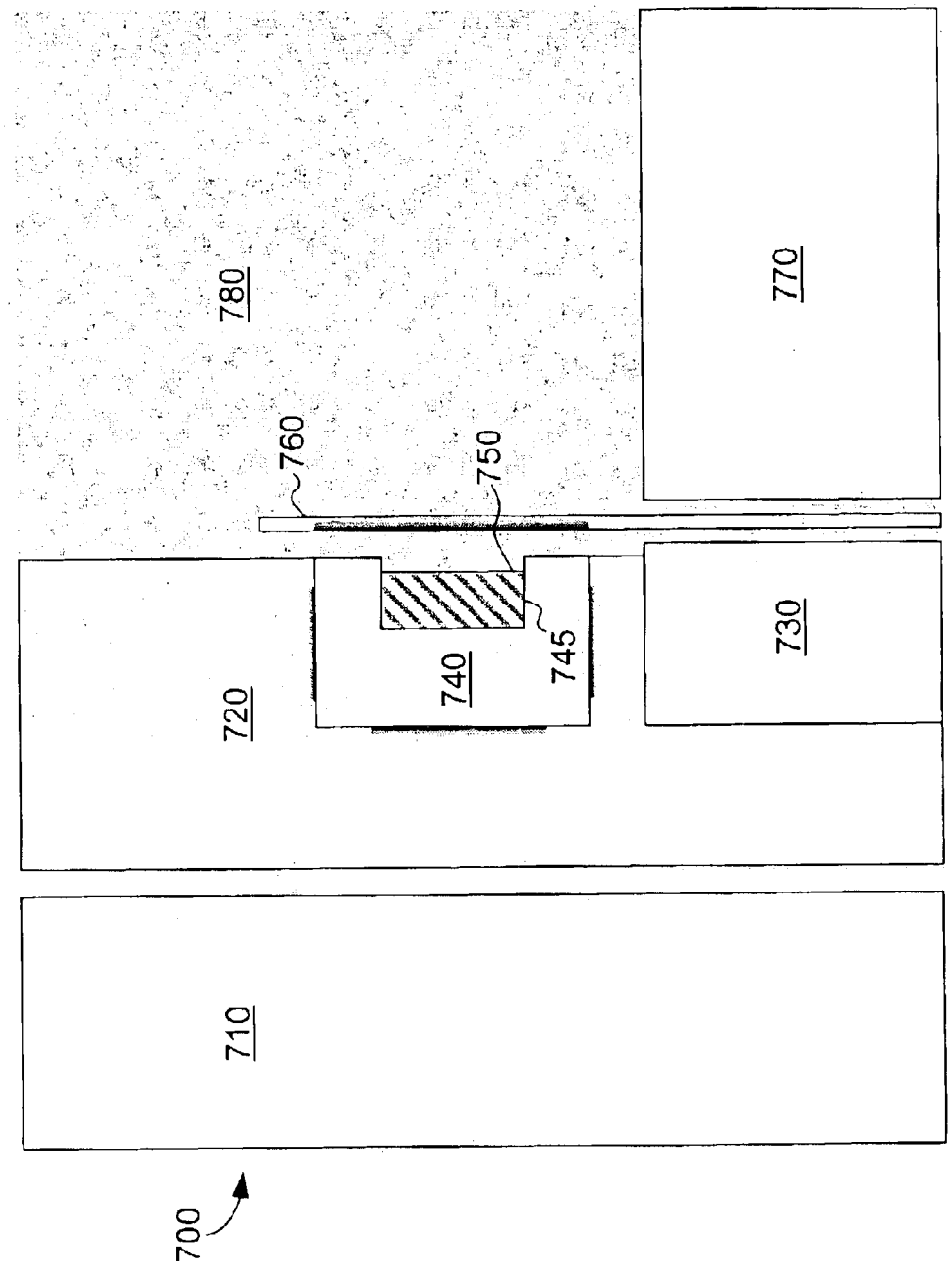
FIG. 7 is a schematic diagram of the relative position of various internal components of a drag cup motor according to an exemplary embodiment of the present invention and their contribution to the resultant eddy current distribution.

FIG. 7 shows an internal portion of a motor 700 according to an exemplary embodiment of the present invention and the relative positions of various components. The relative position of the components shown in FIG. 7 is comparable to the example shown in FIG. 1e, and further shows eddy current densities. As shown in this figure, such eddy current densities are predominately in the drag cup 760 and not other parts of the motor.

As shown in FIG. 7, temperature sensing component 740, which may be, for example, a sensory coil bobbin or a coil former, is positioned on motor core holder 720 such that a relatively small area is formed between the sensing device 740 and an inner surface of drag cup 760. Sensory coil bobbin 740 includes a coil accommodating area 745 that accommodates a coil 750. Temperature sensing component 740 may be, for example, heat-resistant rubber or plastic. Such a coil 750 may be, for example, copper, aluminum wire or the like. The volume 780 is typically filled with air.

During use, as drive shaft 710 rotates with drag cup 760 with respect to other components, an alternating current is applied to coil 750 thereby inducing currents to flow into drag cup 760. These induced currents dissipate energy due to the resistance of drag cup 760, and this energy is supplied by the circuit driving coil 750. As the temperature of drag cup 760 changes, so does its resistance and this alters the energy dissipated by the induced currents. Therefore, by monitoring the power supplied to coil 750, it is possible to accurately determine the temperature of drag cup 760 in the vicinity of coil 750 without having to resort to using temperature sensors within windings 770. Such measurement of the drag cup 760 at such close proximity without resorting to direct contact (which would hinder the operation of the drag cup 760) maximizes temperature sensing without sacrificing drag cup 760 function. Other ways of measuring the eddy currents is possible. Thus, using the exemplary embodiments shown in the figures, in order to measure the electrical activity caused by the eddy currents on the drag cup, it is possible to drive the coil at a fixed voltage and sense current fluctuations, or drive the coil at a fixed current and sense voltage fluctuations.

Care must be taken in the design and calibration of such a system, as the wire of coil 750 itself and other metallic parts in the motor assembly also dissipate energy and such dissipation also changes with fluctuations in temperature. Therefore, the design should be such that induced currents in other metal parts of the assembly are minimized, and the amount of energy dissipated in the wire of coil 750 can be accurately considered and accounted.

Figure 8:
FIG. 8 is a schematic diagram of a graph of non-contact drag cup temperature as well as coil temperature according to an exemplary embodiment of the present invention.

An exemplary graph of the measure of drag cup temperature and coil temperature during a step change in torque is shown in FIG. 8. In the particular example shown, 50% torque was applied at the 60 second time marker and removed (i.e., back to pre-60 second torque of zero) at the 360 second time marker. An advantage of the exemplary embodiments of the present invention is its ability to measure the losses in the coil, which is then subtracted from the total loss to obtain drag cup loss. This loss is converted to temperature. The foregoing is explained in more detail with respect to FIG. 8.

It is noted that coil temperature would be of the same order as stator windings temperature, which shows why estimation of drag cup temperature using temperature changes in the windings is not ideal because the shape of the coil temperature does not follow the drag cup temperature very precisely, with or without offset. The graph of FIG. 8 is merely exemplary and is not intended to be limiting of the abilities and capabilities of exemplary embodiments of the present invention. Different graphs will be produced with motors having different geometries and applied power characteristics.

Figure 9:
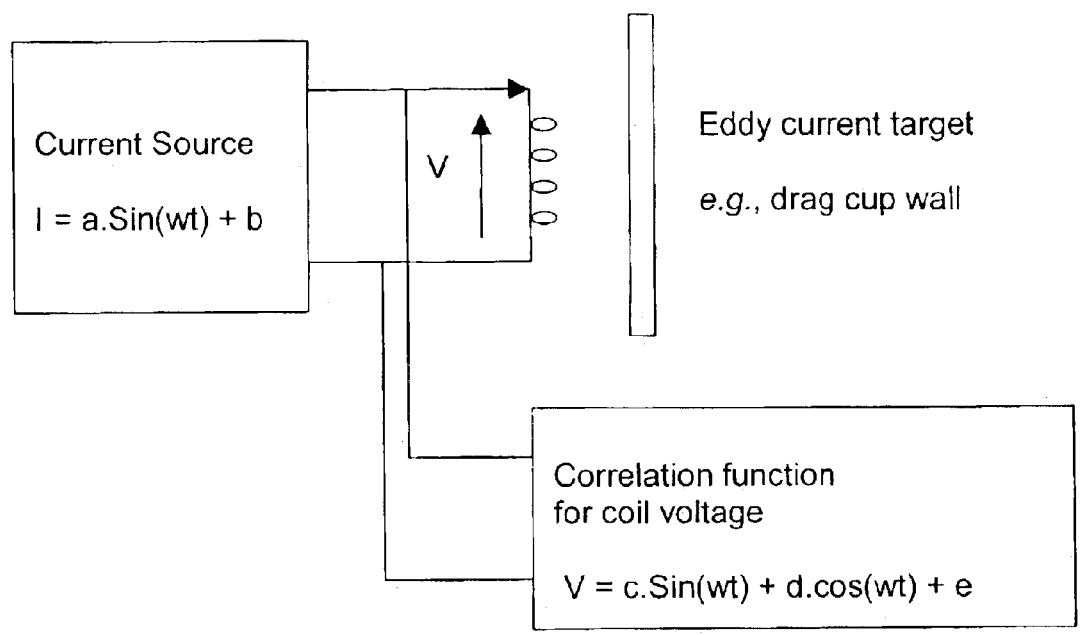
FIG. 9 is a block diagram of a circuit according to an exemplary embodiment of the present invention.

An exemplary embodiment of a circuit that is part of the temperature sensing system according to the present invention is shown in FIG. 9. This circuit is used to sense the temperature of the drag cup by a determination of the presence of eddy currents, which is then used to adjust the torque or speed of the rheometer motor accordingly. In this exemplary embodiment, the applied current includes an alternating component of magnitude "a" and frequency "w" and a static dc component of magnitude "b." This causes a voltage to be developed across the coil of the form described in the correlation function. Magnitudes "c" and "d" are related to the alternating component of magnitude "a" in the applied current. Static dc component "e" is related to the static dc component of magnitude "b" in the applied current.

The total power supplied to the coil due to the alternating component is given by $P_{total}=a.c/2$. To obtain an estimate of the power dissipated due to eddy currents in the target, the alternating component of the power dissipated due to the coil resistance must he subtracted from the total power. The coil resistance can be calculated by $R_{coil}=e/b$. Similarly, the alternating component of the power dissipated due to the coil resistance is $P_{coil}=a^2/2.R_{coil}=a^2/2.e/b$. Therefore, the power dissipated due to the eddy currents in the target is $P_{eddy}=a.c/2-a^2/2.e/b$. This power dissipation due to the eddy currents is used to adjust the actual torque output of a rheometer motor. Other circuits may be used to determine the power dissipation due to eddy currents in the target and are apparent to one having ordinary skill in the art.

The exemplary embodiments shown in the figures may have a variety of shapes and designs. The dimensions of such exemplary embodiments are dependent on the particular rheometer and drag cup motor employed. Thus, there is no particular requirement as to dimensions of particular components of the rheometer including the exemplary embodiments of the temperature sensing component of the present invention. Any configuration is possible as long as it performs the functions as described herein. One exemplary embodiment has the following characteristics:

drag cup outer diameter of 35.62 mm;
drag cup inner diameter of 34.50 mm;
drag cup wall thickness of 0.56 mm;
coil outer diameter of 33.50 mm;
coil inner diameter 30.00 mm;
coil winding thickness of 1.75 mm;
coil length of 5.00 mm (referring to length over which coil was wound, i.e., distance between two outer rims 610)
gap from coil to drag cup of 0.50 mm;
coil wire diameter of 0.20 mm;
number of coil turns of about 150;
alternating component drive frequency "w" of 100000 radians/s;
alternating component current magnitude "a" of 1 mA; and
static dc component current magnitude "b" of 2 mA.

Other dimensions and variable magnitudes are possible and apparent to one having ordinary skill in the art without undue experimentation.

The exemplary devices, systems and methods described herein according to the present invention have many advantages. One such advantage is that the measured and determined temperature of the drag cup is made without hindering the operation of the drag cup or other motor components. By measuring the temperature of the drag cup, the current flow to the motor can be adjusted accordingly such that actual output torque of the motor is maintained relatively constant.

Other advantages of devices, systems and methods according to the present invention are possible and are apparent to one having ordinary skill in the art.

In describing representative embodiments of the invention, the specification may have presented the method and/or process of the invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the invention should not be limited to the performance of their steps in the order written, and one skilled in the art can readily appreciate that the sequences may be varied and still remain within the spirit and scope of the invention.

The foregoing disclosure of the embodiments of the invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

What is claimed is:

1. A drag cup motor, comprising:
    a motor core holder;
    motor windings disposed around the motor core holder;
    a drag cup surrounding and rotatable about the motor core holder; and
    a coil mounted around the motor core holder and in communication with a source of current, wherein the coil is in close enough proximity to the drag cup such that the coil can sense the temperature of the drag cup through fluctuations in electrical activity across the coil.

2. The drag cup motor of claim 1, wherein the electrical activity comprises voltage.

3. The drag cup motor of claim 1, wherein the electrical activity comprises current flow.

4. The drag cup motor of claim 1, wherein the drag cup is cylindrical and has an interior portion.

5. The drag cup motor of claim 4, wherein the coil is located within the interior portion of the drag cup.

6. The drag cup motor of claim 1, wherein the coil is wound on a removable coil holder.

7. The drag cup motor of claim 1, wherein the coil comprises copper wire.

8. A drag cup motor in a rheometer, comprising:
    a motor core holder;
    motor windings disposed around the motor core holder;
    a drag cup surrounding and rotatable about the motor core holder; and
    a coil wound around a coil former that is mounted on the motor core holder, the coil being in communication with a source of current, wherein the coil is in close enough proximity to the drag cup such that the coil can sense the temperature of the drag cup through fluctuations in electrical activity across the coil.

9. The drag cup motor of claim 8, wherein the electrical activity comprises voltage.

10. The drag cup motor of claim 8, wherein the electrical activity comprises current flow.

11. The drag cup motor of claim 8, wherein the drag cup is cylindrical and has an interior portion.

12. The drag cup motor of claim 11, wherein the coil is located within the interior portion of the drag cup.

13. The drag cup motor of claim 8, wherein the coil is wound on a removable coil holder.

14. A device for sensing the temperature of a drag cup in a motor of a rheometer, the device comprising:
    means for sensing temperature, wherein the means for sensing temperature is in contact with a source of current; and
    a drag cup located within a motor of a rheometer and in close enough proximity to the means for sensing temperature such that the means for sensing temperature senses the temperature of the drag cup through fluctuations in electrical activity.

15. The device of claim 14, wherein the electrical activity comprises voltage.

16. The device of claim 14, wherein the electrical activity comprises current flow.

17. The device of claim 14, wherein the drag cup is cylindrical and has an interior portion.

18. The device of claim 17, wherein the means for sensing temperature is located within the interior portion of the drag cup.

19. The device of claim 14, wherein the means for sensing temperature is removable.

20. The device of claim 14, wherein the means for sensing temperature is located at an end portion of the drag cup.

21. The device of claim 14, wherein the means for sensing temperature is monitored for changes in voltage.

22. A method of adjusting winding current in a drag cup motor to compensate for changes in torque due to changes in drag cup temperature, the method comprising:
   operating the drag cup motor;
   supplying current to a coil that is wound adjacent an internal periphery of the drag cup;
   determining changes in torque due to changes in temperature of the drag cup by sensing fluctuations in voltage across the coil caused by changes in temperature of the drag cup; and
   adjusting winding current to compensate for the changes in torque.

23. The method of claim 22, wherein the drag cup is cylindrical and has an interior portion.

24. The method of claim 22, wherein the coil is wound on a coil former.

25. The method of claim 22, wherein the coil is positioned toward one end of the drag cup.

26. The method of claim 22, wherein the coil comprises copper wire.

* * * * *